United States Patent [19]

Siemensmeyer et al.

[11] Patent Number: 5,695,681
[45] Date of Patent: Dec. 9, 1997

[54] LIQUID-CRYSTALLINE ALLENES

[75] Inventors: Karl Siemensmeyer, Frankenthal; Carsten Tschierske; Kerstin Zab, both of Halle, all of Germany

[73] Assignee: BASF Aktiengesellschaft, Ludwigshafen, Germany

[21] Appl. No.: 624,918

[22] Filed: Mar. 27, 1996

[30] Foreign Application Priority Data

Mar. 30, 1995 [DE] Germany ............ 195 11 448.5

[51] Int. Cl.[6] ............ C09K 19/52; C09K 19/34; C07D 285/12
[52] U.S. Cl. ............ 252/299.01; 252/299.61; 252/299.63; 252/299.64; 252/299.65; 252/299.66; 252/299.67; 428/1; 548/136
[58] Field of Search ............ 252/299.01, 299.61, 252/299.63, 299.64, 299.65, 299.66, 299.67; 428/1; 548/136

[56] References Cited

PUBLICATIONS

CA 124: 8209, 1996.
CA 116: 82910, 1992.
CA 114: 80660, 1991.

*Primary Examiner*—Shean Wu
*Attorney, Agent, or Firm*—Oblon, Spivak, McClelland, Maier & Neustadt, P.C.

[57] ABSTRACT

Liquid-crystalline allenes of the formula I

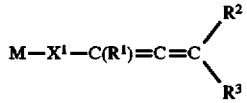

where
M is a mesogenic group,
$R^1$ and $R^2$ are hydrogen or a C-organic radical having 1–8 carbon atoms,
$R^3$ is a C-organic radical having 1–30 carbon atoms,
$X^1$ is $-(CH_2)_q-O-(CH_2)_p-$,
$-(CH_2)_q-NR^4-(CH_2)_p-$,
$-(CH_2)_q-CO-O-(CH_2)_p-$,
$-(CH_2)_q-O-CO-(CH_2)_p-$,
$-(CH_2)_q-CO-NR^4-(CH_2)_p-$ or
$-(CH_2)_q-NR^4-CO-(CH_2)_p-$,
$R^4$ is hydrogen or an alkyl radical having 1–4 carbon atoms,
p is from 1 to 20, and
q is from 0 to 20,
where the definitions of $R^2$ and $R^3$ can also be interchanged, are used in optical display elements.

9 Claims, No Drawings

LIQUID-CRYSTALLINE ALLENES

BACKGROUND OF THE INVENTION

FIELD OF THE INVENTION

The present invention relates to novel liquid-crystalline allenes of the formula I

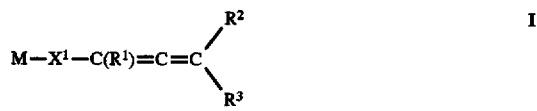

where
M is a mesogenic group,
$R^1$ and $R^2$ are hydrogen or a C-organic radical having 1–8 carbon atoms,
$R^3$ is a C-organic radical having 1–30 carbon atoms,
$X^1$ is —$(CH_2)_q$—O—$(CH_2)_p$—,
—$(CH_2)_q$—$NR^4$—$(CH_2)_p$—,
—$(CH_2)_q$—CO—O—$(CH_2)_p$—,
—$(CH_2)_q$—O—CO—$(CH_2)_p$—,
—$(CH_2)_q$—CO—$NR^4$—$(CH_2)_p$— or
—$(CH_2)_q$—$NR^4$—CO—$(CH_2)_p$—,
$R^4$ is hydrogen or an alkyl radical having 1–4 carbon atoms,
p is from 1 to 20, and
q is from 0 to 20,
where the definitions of $R^2$ and $R^3$ can also be interchanged.

The present invention furthermore relates to the preparation of the novel liquid-crystalline compounds, to novel allenes as intermediates for coupling to mesogenic groups, and to the use of liquid-crystalline compounds in optical display elements, in optical, electronic and electro-optical storage media, in electrophotographic instruments and in light-reflecting layers.

DISCUSSION OF THE BACKGROUND

As is known, liquid-crystalline compounds are employed for many purposes in the electro-optical field. Mention may be made here by way of example of optical storage systems (DE-A-38 27 603 and DE-A-39 17 196), electrophotography (DE-A-39 30 667), liquid-crystalline display elements (Mol. Cryst. Liq. Cryst. 114 (1990) 151) and, in the case of ferroelectric liquid-crystalline media, electrical storage systems (Ferroelectrics, 104 (1990) 241). Ferroelectric materials exhibit permanent polarization when they are introduced into an electric field, ie. they retain their alignment after the field has been switched off again. The phenomenon of ferroelectricity is also exhibited by certain liquid-crystalline compounds which have a chiral structure.

In the layer structure of ferroelectric, smectic liquid-crystalline C phases (known as $S_c^*$ phases), the long molecular axes are inclined to the layer normals Z within each individual layer. The direction of this inclination is given by the director n. $S_c^*$ phases have two stable states with different directions of n, between which switching can be effected by applying an electric field (electro-optical effect).

Ferroelectric liquid crystals are used in particular in electro-optical display elements which operate on the principle of the surface stabilized ferroelectric liquid crystal (SSFLC). These display elements generally contain mixtures of liquid-crystalline compounds which are either themselves chiral or in which chirality is induced by the presence of chiral substances. The properties of the liquid-crystalline compounds in these display elements are subject to severe demands. A relatively low spontaneous polarization and low rotational viscosity are desirable in order to achieve fast response times. In addition, a broad phase width is desired for the $S_c^*$ phase. With respect to these properties, known liquid-crystalline compounds are unsatisfactory.

SUMMARY OF THE INVENTION

It is an object of the present invention to provide novel ferroelectric liquid crystals having broad enantiotropic liquid-crystalline phases which induce a low spontaneous polarization and simultaneously have low rotational viscosity.

We have found that this object is achieved by the liquid-crystalline allenes mentioned at the outset.

DESCRIPTION OF THE INVENTION

Through the allene group, a chiral group is introduced into the mesogenic compound, enabling the particularly desired ferroelectric liquid-crystalline properties to arise. Particular preference is therefore given to novel compounds which contain only one enantiomer or at least a mixture of the two enantiomers in which the enantiomer ratio is greater than 60:40.

The substituents $R^1$ and $R^2$ can be hydrogen or C-organic radicals having 1–8 carbon atoms. Besides pure alkyl groups, chains interrupted by oxygen or nitrogen, for example —$CH_2$—$CH_2$—O—$CH_2$—$CH_3$ or $CH_2$—$CH_2$—NH—$CH_2$—$CH_3$, are also suitable. However, preference is given to short alkyl radicals, such as methyl, ethyl and propyl, and hydrogen.

$R^3$ and $R^5$ are C-organic radicals having 1–30 carbon atoms. Preference is given to radicals of the type which have an essentially linear structure, ie., for example, straight-chain alkyl or alkyl which is interrupted by oxygen, nitrogen, ester or amide groups. Preference is given to alkyl radicals having 4–12 carbon atoms, particularly preferably those having 5–9 carbon atoms, very particularly preferably n-heptyl.

The liquid-crystalline compounds I are prepared from allenes of the formula II

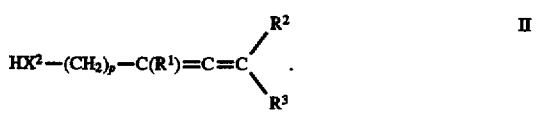

These allenes II carry, for coupling to the mesogenic group M, a hydroxyl, amino or carboxyl group which is bonded to the allene group via a —$(CH_2)_p$— group, where p is a number from 1 to 20, preferably from 1 to 8, particularly preferably 1. Particular preference is given to the allene intermediate

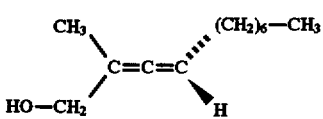

and its enantiomer.

Allenes of the formula IIa

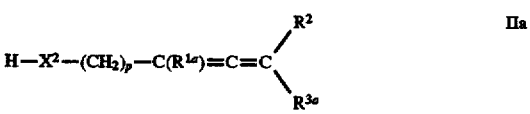

are of particular importance as intermediates for the preparation of the liquid-crystalline allenes of the formula I.

Preferred radicals $R^{3a}$ are those mentioned above for $R^3$, but having not more than 6 carbon atoms. Preference is given to linear alkyl groups having 7 to 11 carbon atoms, particularly preferably n-heptyl.

Since chiral allenes exhibit particular liquid-crystalline properties, they are also particularly preferred for these intermediates. Particular preference is likewise given to mixtures of enantiomers in which one enantiomer is present in an excess of at least 60:40.

The mesogenic group M preferably has the structure Ia

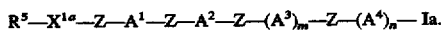 Ia.

It has an essentially linear structure and preferably comprises 2 to 4 ring groups A linked to one another via bridges Z. Examples of suitable ring groups A are substituted and unsubstituted iso- and heteroaromatic groups, such as

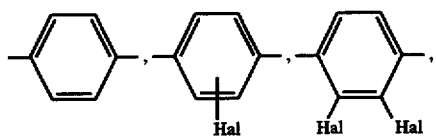

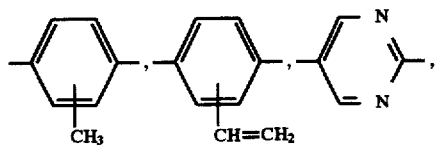

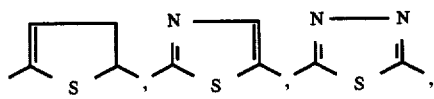

where Hal is halogen or pseudohalogen, particularly preferably F, Cl or CN, and nonaromatic ring structures, such as

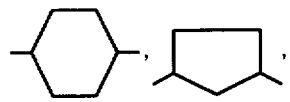

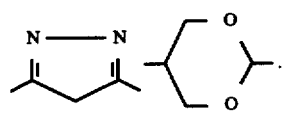

Examples of particularly preferred

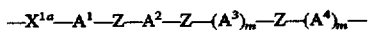

moieties are

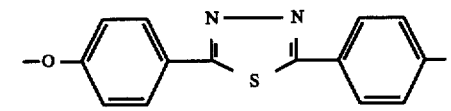

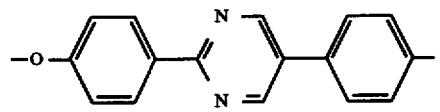

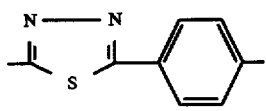

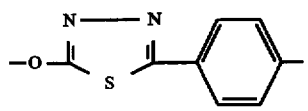

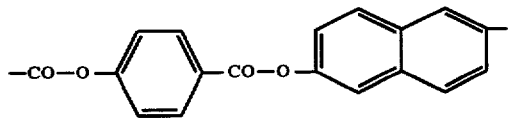

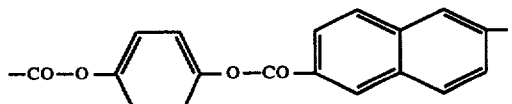

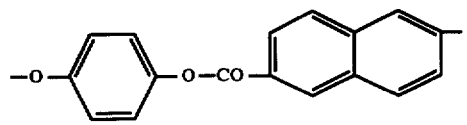

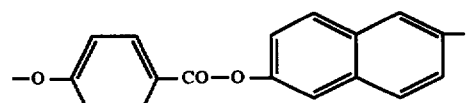

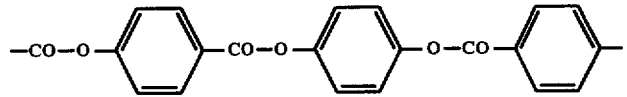

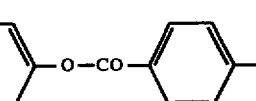

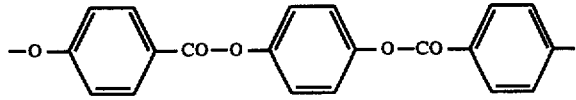

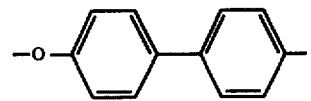

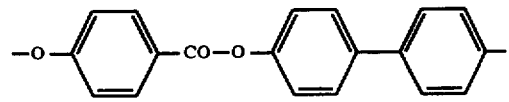

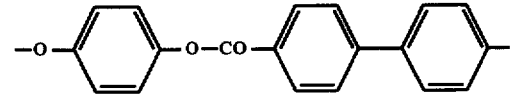

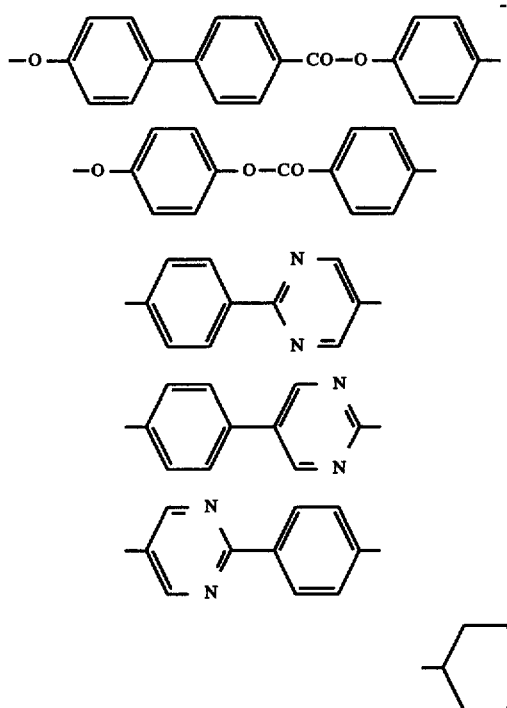

The liquid-crystalline allenes are preferably prepared by synthesizing the mesogenic group and the allene moiety separately. The allene moiety carries, as functional coupling group, a hydroxyl, amino or carboxyl group, coupling via a hydroxyl group with formation of an ether bond to the mesogenic group being preferred.

The allenes of the formula II are obtainable in a manner known per se via several steps, for example in the following sequence starting from the corresponding alkynols (for $X^2$=—$NR^4$— or —O—CO—, starting from the corresponding alkynamines or alkynecarboxylic acids).

a) Protection of the alkynol (see, for example, J. Org. Chem. 47 (1982) 2549)

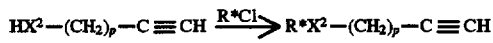

R* is a protecting group, preferably a silyl group, particularly preferably tert-butyldiphenylsilyl.

b) Reaction of the alkyne with a carbonyl compound (see, for example, J. Org. Chem. 40 (1975) 2250)

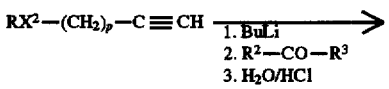

In order to prepare optically active allenes, the racemic tertiary alcohols can either be separated into the enantiomers by known methods and then brominated as described under e) or, in the case where the carbonyl compound employed is an aldehyde, reacted as follows:

c) Oxidation of the alcohol to the ketone (see, for example, Tetrahedron Lett. 31 (1975) 2647)

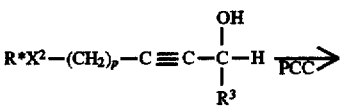

The oxidation can be carried out using various oxidants, preferably pyridinium chlorochromate (PCC).

d) Reduction of the ketone, preferably using an optically active reducing agent (see, for example, Tetrahedron 40 (1984) 1371)

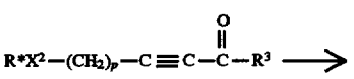

The reducing agents are preferably optically active boranes, particularly preferably optically active B-3-pinanyl-9-borabicyclo[3.3.1]nonane (Alpine-Borane).

e) Bromination of the alcohol (see, for example, J. Org. Chem. 56 (1991) 1083)

-continued

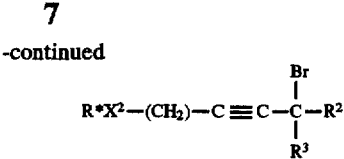

The brominating agent is preferably CBr₄ in the presence of triphenylphosphine. R² here is hydrogen if an aldehyde was employed in step b). If a ketone was employed, R² is a C-organic radical having 1-8 carbon atoms.

f) Conversion of the alkynyl bromide into a substituted allene (see, for example, J. Org. Chem. 53 (1978) 1389)

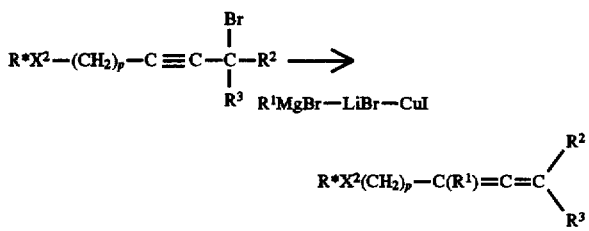

The allene formation is preferably accomplished with the aid of a cuprate, which is formed, for example, in situ from CuI and a Grignard compound. This reaction allows a desired substituent R¹ to be introduced into the allene.

g) Removal of the protecting group (see, for example, J. Org. Chem. 56 (1991) 1083)

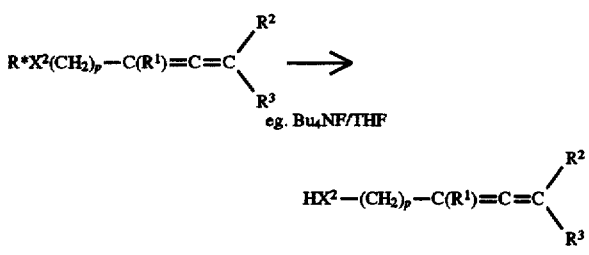

The silyl protecting group is preferably removed using tetrabutylammonium fluoride.

h) Coupling of the allene to a mesogenic compound

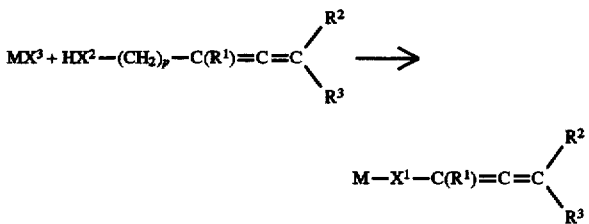

The suitable condensation agent for coupling of the allene to the mesogenic group depends on the nature of the functional groups provided for the coupling.

An alcohol is reacted with a phenolic hydroxyl group of the mesogenic group, preferably by means of diethyl azodicarboxylate/triphenylphosphine. For coupling of a hydroxyl or amino group to a carboxyl group, use can be made, for example, of carbodiimides or carbonyldiimidazole.

The novel liquid-crystalline allenes can be used alone or in combination with other compounds. In particular, combinations with substances which modify the temperature range or width of the liquid-crystalline phases in a desired manner are advantageous.

Liquid-crystalline allenes are used in the production of electro-optical display elements, in optical, electronic and electro-optical storage media, in electrophotographic instruments and in light-reflecting layers. A particularly preferred use of the novel compounds is in SSFLC displays, since, through their ferroelectric properties, their relatively low spontaneous polarization and low rotational viscosity, they have a particularly favorable switching behavior.

EXAMPLES

Example 1

Preparation of (S)-2-methyl-1-{4-[5-(4-octyloxyphenyl)-1,3,4-thiadiazol-2-yl]phenoxy}undeca-2,3-diene [9a]

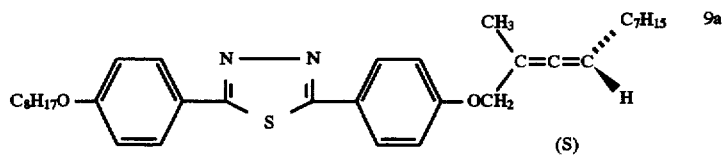

a) Preparation of rac-1-(tert-butyldiphenylsilyloxy)undec-2-yn-4-ol [2]

15.9 g (54 mmol) of silyl-protected propargyl alcohol in 80 ml of abs. THF were cooled to −78° C., and 33 ml (3.5 g, 54 mmol) of n-butyllithium (1.6M in hexane) were added under argon. After 30 minutes, 6.1 g (49 mmol) of octanal in 20 ml of abs. THF were added dropwise. After a further 3 hours, the mixture was hydrolyzed at 0° C. using 80 ml of 10% strength by weight hydrochloric acid. Work-up was carried out by ether extraction and column chromatography. Yield: 65% b) Preparation of 1-(tert-butyldiphenylsilyloxy)undec-2-yn-4-one [3]

13 g (30 mmol) of [2] in 30 ml of abs. dichloromethane were mixed at room temperature with a suspension of 12.9 g (60 mmol) of pyridinium chlorochromate in 60 ml of abs. dichloromethane. After the mixture had been stirred for 4 hours, 300 ml of n-pentane were added. The solution was decanted, the solid was washed with pentane, and the combined organic extracts were filtered and concentrated. The residue was purified by column chromatography. Yield: 70% c) Preparation of (R)-1-(tert-butyldiphenylsilyloxy)undec-2-yn-4-one [4]

3 g (7.1 mmol) of [3] were mixed at 0° C. under argon with 28.6 ml (14.2 mmol) of a 0.5 molar solution of (R)-Alpine-Borane in THF, and the mixture was then stirred at room temperature for 4 days. 0.56 ml (10 mmol) of freshly distilled acetaldehyde were subsequently added dropwise, and the mixture was stirred for a further hour. The α-pinene liberated was then distilled off in vacuo. 5 ml of abs. THF, 3 ml of 3M NaOH and 5 ml of 30% strength by weight $H_2O_2$ solution were then added, and the mixture was stirred at 40° C. for 3 hours. Work-up was carried out by ether extraction and 15 column chromatography. Yield: 63% Enantiomeric purity: 88% e.e.

d) Preparation of (S)-4-bromo-1-(tert-butyldiphenylsilyloxy) undec-2-yne [5]

3.6 g (8.5 mmol) of [4], 0.77 g (9.7 mmol) of abs. pyridine and 5.4 g (20 mmol) of triphenylphosphine were dissolved in 50 ml of abs. THF, and the mixture was mixed at 20° C. with stirring with a solution of 3.2 g (9.7 mmol) of tetrabromo-methane and 0.1 ml of abs. pyridine in 20 ml of abs. THF. The mixture was stirred under argon for 2 hours, and 150 ml of hexane were then added. The solid which precipitated was filtered off, and the solution was washed twice in succession with 10% strength hydrochloric acid, saturated $NaHCO_3$ solution and saturated NaCl solution. The solution was then dried over $Na_2SO_4$ and the solvent was distilled off under reduced pressure. The crude product was purified by column chromatography. Yield: 63% e) Preparation of (S)-1-(tert-butyldiphenylsilyloxy)-2-methyl-undeca-2,3-diene [6]

8 ml (24 mmol, 3M in ether) of methylmagnesium bromide were added dropwise at 0° C. under an argon atmosphere to a vigorously stirred suspension of 2.1 g (24 mmol) of lithium bromide and 4.6 g (24 mmol) of copper(I) iodide in 240 ml of abs. THF. The reaction mixture was stirred at 0° C. for 15 minutes, and 3.9 g (8 mmol) of [5], dissolved in abs. THF, were then added. After a further hour at 0° C., 50 ml of saturated $NH_4Cl$ solution were added, the solid which precipitated was filtered off, and the organic phase was freed from solvent under reduced pressure. Work-up was carried out by ether extraction and column chromatography. Yield: 80% f) Preparation of (S)-2-methylundeca-2,3-dien-1-ol [7]

16.5 ml (16.5 mmol) of tetra-n-butylammonium fluoride (1M in THF) were added dropwise under argon to a solution of 2.3 g (5.5 mmol) of [6] in 10 ml of abs. THF, and the mixture was stirred for 12 hours. The solution was subsequently concentrated and worked up by dichloromethane extraction and column chromatography. Yield: 70% Enantiomeric purity: 52% e.e.

g) Preparation of (S)-2-methyl-1-{4-[5-(4-octyloxyphenyl)-1,3,4-thiadiazol-2-yl]phenoxy}undeca-2,3-diene [9a]

0.2 g (1 mmol) of [7], 0.26 g (0.67 mmol) of 4-[5-(4-octyl-oxyphenyl)-1,3,4-thiadiazol-2-yl]phenol [8a] and 0.26 g (1 mmol) of dry triphenylphosphine were dissolved in 10 ml of abs. THF, and a solution of 0.17 g (1 mmol) of diethyl azodicarboxylate in 10 ml of abs. THF was added with ice cooling and stirring. The mixture was stirred at room temperature for 20 hours, and the solvent was subsequently stripped off under reduced pressure. Purification was carried out by recrystallization from methanol/water (10:1) and subsequently from methanol/chloroform (3:1). Yield: 28%

Example 2

Preparation of racemic 9a

The racemic compound was obtained by direct reaction of the protected propargyl alcohol [2] as described in Example 1d to give the bromide [rac-5] and analogous further reactions.

Example 3

Preparation of

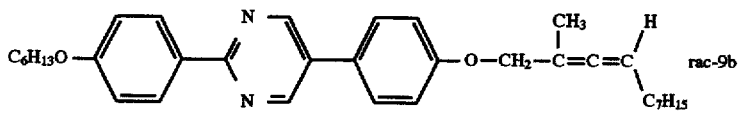

The compound was obtained by condensation of the allene alcohol 2-methylundeca-2,3-dien-1-ol (rac-7, obtainable analogously to Example 1f) with the mesogenic compound

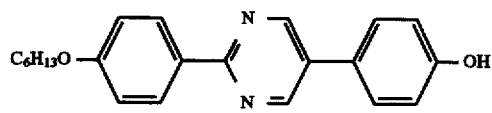

analogously to the reaction described in Example 1g.

Example 4

The phase behavior of the compounds described in Examples 1 to 3 was investigated. For liquid-crystalline compounds, in particular when used in optical display elements, a broad temperature range of the desired liquid-crystalline phase, in particular of the $S_c$ or $S_c^*$ phase, is desirable. In the present cases, favorable $S_c$ or $S_c^*$ phase widths of approx. 30–40° C. were found.

The phase transition temperatures were determined as usual using a polarizing microscope (Leitz Ortholux II pol) in combination with a microscope heating stage (Mettler FP 800/82).

The abbreviations have the following meanings:

| | |
|---|---|
| cr = | crystalline |
| $S_c$ = | smectic liquid-crystalline |
| $S_c^*$ = | ferroelectric smectic liquid-crystalline |
| N = | nematic |
| N* = | ferroelectric nematic |
| BP = | blue phase |
| is = | isotropic |

} liquid-crystalline phases

The following phase transition temperatures were measured for the compounds of Examples 1 to 3:

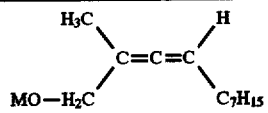

| M | | Phase | Temperature range [°C.] |
|---|---|---|---|
| (S)-9a (see Ex. 1) C₈H₁₇O— |  | Cr S_c* N* BP is | <67 67–99 99–101 101–102 >102 |
| rac-9a (see Ex. 2) C₈H₁₇O— | | Cr S_c N is | <64 64–96 96–99 >99 |
| rac-9b (see Ex. 3) C₆H₁₃O— | | Cr S_c N is | <59 59–95 95–97 >97 |

We claim:

1. A liquid-crystalline allene of the formula I

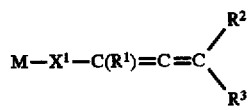

where
M is a mesogenic group,
$R^1$ is hydrogen or a C-organic radical having 1–8 carbon atoms,
one of $R^2$ and $R^3$ is hydrogen or a C-organic radical having 1–8 carbon atoms, and the other of $R^2$ and $R^3$ is a C-organic radical having 1–30 carbon atoms,
$X^1$ is —(CH₂)_q—O—(CH₂)_p—,
—(CH₂)_q—NR⁴—(CH₂)_p—,
—(CH₂)_q—CO—O—(CH₂)_p—,
—(CH₂)_q—O—CO—(CH₂)_p—,
—(CH₂)_q—CO—NR⁴—(CH₂)_p— or
—(CH₂)_q—NR⁴—CO—(CH₂)_p—,
$R^4$ is hydrogen or an alkyl radical having 1–4 carbon atoms,
p is from 1 to 20, and
q is from 0 to 20.

2. A liquid-crystalline allene as claimed in claim 1, where M is a radical of the formula Ia $$R^5-X^{1a}-Z-A^1-Z-A^2-Z-(A^3)_m-Z-(A^4)_n-\quad Ia$$

where
$A^1$–$A^4$ are iso- or heteroaromatic or iso- or heterocycloaliphatic groups which optionally themselves carry substituents,
$R^5$ is a C-organic radical having 1–30 carbon atoms,
$X^{1a}$ is $X^1$ or a chemical bond,
Z are identical or different bridges having the structure
—CO—O—, —O—CO—, —CH=CH—, —N=N—,
—CH=N—, —N=CH—,
—CO—NR⁴—, —NR⁴—CO—, —CH₂—O—,
—O—CH₂— or a chemical bond, and
m and n are 0 or 1.

3. A liquid-crystalline allene as claimed in claim 2, where one of the radicals $A^1$ to $A^4$ is a heteroaromatic radical, and the other radicals are 1,4-phenylene.

4. A liquid-crystalline allene as claimed in claim 3, where the $$-A^1-Z-A^2-Z-(A^3)_m-Z-(A^4)_n-$$

group is

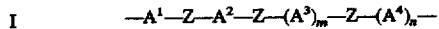

5. In an optical display element, the improvement wherein the optical display element comprises a liquid-crystalline allene as claimed in claim 1.

6. In an electro-optical storage medium, the improvement wherein the electro-optical storage medium comprises a liquid-crystalline allene as claimed in claim 1.

7. In an electrophotographic instrument, the improvement wherein the electrophotographic instrument comprises a liquid-crystalline allene as claimed in claim 1.

8. In a light-reflecting layer, the improvement wherein the light-reflecting layer comprises a liquid-crystalline allene as claimed in claim 1.

9. A process for the preparation of a liquid-crystalline allene as claimed in claim 1, which comprises reacting an allene of the formula II

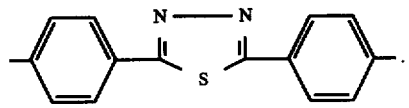

where $R^1$, $R^2$, $R^3$ and p are as defined in claim 1, and $X^2$ is —O—, —NR⁴— or —O—CO—, with a compound of the formula III $$M-X^3 \quad III$$

where $X^3$ is a reactive group which can react with $HX^2$— to form an ether, amino, ester or amide link.

* * * * *